(12) United States Patent
Petersen et al.

(10) Patent No.: US 6,291,689 B1
(45) Date of Patent: Sep. 18, 2001

(54) METHOD FOR THE PREPARATION OF CITALOPRAM

(75) Inventors: Hans Petersen, Vanløse; Klaus Peter Bøgesø, Hørsholm; Michael Bech Sommer, Bagsvaerd, all of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/565,061

(22) Filed: May 3, 2000

Related U.S. Application Data

(63) Continuation of application No. PCT/DK97/00511, filed on Nov. 10, 1997.

(51) Int. Cl.[7] ............. C07D 307/87; C07C 255/50; C07C 233/65; C07C 69/76
(52) U.S. Cl. ............. 549/467; 558/423; 560/57; 564/171
(58) Field of Search ............. 549/467; 558/423; 560/57; 564/171

(56) References Cited

U.S. PATENT DOCUMENTS

| | | | |
|---|---|---|---|
| 3,467,675 | 9/1969 | Petersen et al. | 260/346.2 |
| 4,136,193 | * 1/1979 | Bogeso et al. | 549/467 |
| 5,814,636 | * 9/1998 | Katano et al. | 514/252 |

FOREIGN PATENT DOCUMENTS

| | | | |
|---|---|---|---|
| 0 171 943 | 2/1986 | (EP) | C07C/121/80 |
| WO 98/19511 | 5/1998 | (WO) | |
| WO 98/19512 | 5/1998 | (WO) | |
| WO 98/19513 | 5/1998 | (WO) | |

OTHER PUBLICATIONS

House, Modern Synthetic Reactions, W.A > Benjamin, Inc., New York, p. 184–189, 1965.*
Perregaard et al., "σ Ligands with Subnanomolar Affinity and Preference for the $\sigma_2$ Binding Site. 1. 3–ω–aminoalkyl)–1H–indoles," *J. Med. Chem.* 38: 1998–2008 (1995).

Allan J. Bigler et al.; Quantitative Structure–Activity Relationships in A Series of Selective 5–HT Uptake Inhibitors; May–Jun. 1977; 12: No. 3, pp. 289–295; Eur. J. Med. Chem.—Chem. Therapeutica.

* cited by examiner

*Primary Examiner*—Bernard Dentz
(74) *Attorney, Agent, or Firm*—Darby & Darby

(57) ABSTRACT

A method for the preparation of citalopram is described comprising reduction of the oxo group of a compound of formula (IV),

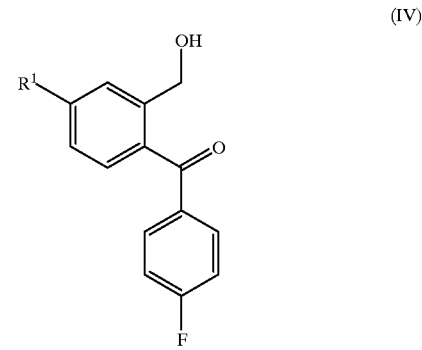

(IV)

wherein $R^1$ is CN, $C_{1-6}$ alkyloxycarbonyl or $C_{1-6}$ alkylaminocarbonyl, ring closure of the resulting hydroxy compound thereby obtaining the corresponding 1-(4-fluorophenyl)-1,3-dihydroisobenzofuran, then if $R^1$ is cyano using it directly in the next step and if $R^1$ is $C_{1-6}$ alkyloxycarbonyl or $C_{1-6}$ alkylaminocarbonyl, conversion of the compound to the corresponding compound wherein $R^1$ is a cyano; and alkylation of the resulting 5-cyano compound with 3-dimethyl-aminopropylhalogenide in basic conditions thereby obtaining citalopram.

30 Claims, No Drawings

METHOD FOR THE PREPARATION OF CITALOPRAM

This is a continuation of International Application No. PCT/DK97/00511, filed Nov. 10, 1997, the entire disclosure of which is incorporated herein by reference.

The present invention relates to a method for the preparation of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

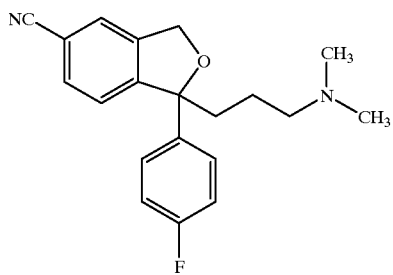

Formula I

It is a selective, centrally active serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,271 corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

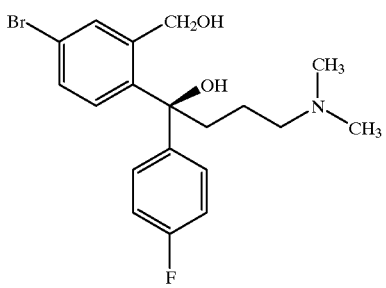

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

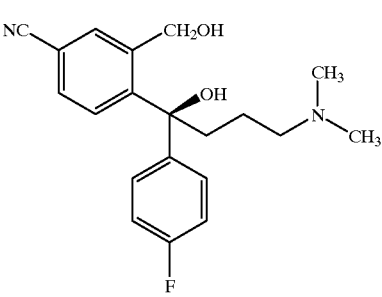

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Finally, methods of preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram comprising the steps of:

a) reduction of a compound of Formula IV

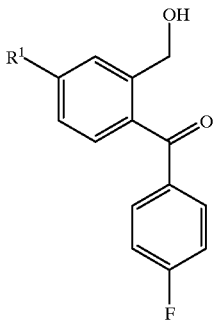

Formula IV wherein $R^1$ is CN, $C_{1-6}$ alkyloxycarbonyl or $C_{1-6}$ alkylaminocarbonyl, b) effecting ring closure of the resulting compound of Formula V

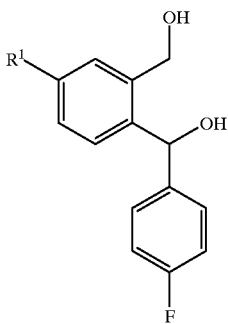

Formula V wherein $R^1$ is as defined above thereby obtaining a compound of Formula VI

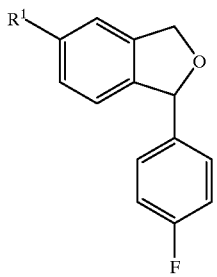

Formula VI wherein $R^1$ is as defined above c) then if $R^1$ is cyano using the compound of Formula VI directly in the next step and if $R^1$ is $C_{1-6}$ alkyloxycarbonyl or $C_{1-6}$ alkylaminocarbonyl, converting the compound of Formula VI to the corresponding compound wherein $R^1$ is cyano; and d) alkylating the resulting 5-cyano compound of formula VI ($R^1$=CN) with 3-dimethyl-aminopropylhalogenid in basic conditions thereby obtaining citalopram,

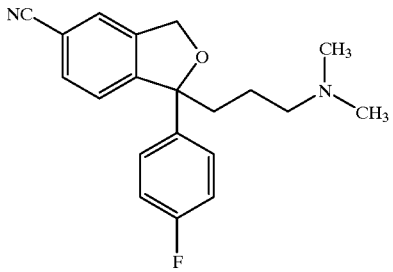

Formula I which is isolated as the base or a pharmaceutically acceptable salt thereof.

In another aspect, the present invention provides the novel intermediates of Formula V.

A further aspect of the invention relates to the novel intermediate for preparation of citalopram of Formula VI wherein $R^1$ is $C_{1-6}$ alkoxycarbonyl or $C_{1-6}$ alkylaminocarbonyl.

In yet another aspect, the present invention relates to an antidepressant pharmaceutical composition comprising citalopram manufactured by the process of the invention.

Throughout the specification and claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl.

The 3-dimethylaminopropylhalogenide used may be the chloride, bromide or iodide, preferably the chloride.

The reduction of the compound of Formula IV may be performed with any convenient reducing agent, preferably by $NaBH_4$ in an alcohol, such as ethanol or methanol in basic conditions or with zink in aqueous acetic acid.

The ring closure of the compound of Formula V may be effected by an acid or via a labile ester with a base. Acidic ring closure is performed by an inorganic acid, such as a sulfuric or phosphoric acid, or an organic acid, such as methylsulfonic, p-toluenesulfonic or trifluoroacetic acid. The basic ring closure may be performed via a labile ester, such as the methane sulfonyl, p-toluene sulfonyl, 10-camphorsulfonyl, trifluoroacetyl or trifluoromethane-sulfonyl ester with addition of a base, such as triethyl amine, dimethylaniline, pyridine, etc. The reaction is performed in an inert solvent, preferably with cooling, in particular about 0° C. and is preferably carried out by a one-pot procedure, i.e. with esterification and simultaneous addition of the base.

When $R^1$ is an alkylaminocarbonyl group, the conversion to cyano may be performed by conventional nitril synthesis. Thus, the amide of Formula V wherein $R^1$ is an alkylaminocarbonyl group is preferably converted to the cyano compound, i.e. citalopram, by reaction with a dehydrating agent, most preferably thionyl chloride or phosphor pentachloride.

When $R^1$ is an alkyloxycarbonyl group, the conversion to cyano is preferably performed via the corresponding amide group which is then converted to the cyano group in the same way as compounds of Formula VI wherein $R^1$ is an alkylaminocarbonyl group.

The reaction of alkyloxycarbonyl to amide is carried out by hydrolysis with an acid or a base and subsequent conversion to acid chloride and amidation by reaction with ammonia or an alkylamine, preferably t-butyl amine. Acid hydrolysis may be performed by use of any suitable acid, such as HBr, HCl, HBr/acetic acid. Basic hydrolysis may be performed with any suitable base, such as $K_2CO_3$, NaOH, KOH, etc. The conversion to amide may also be obtained by reaction of the ester ($R^1$ is an alkyloxycarbonyl group) with ammonia or an alkylamine under pressure and heating. The amide obtained is converted to the cyano group as described above.

Alternatively, an ester, i.e. a compound of Formula VI wherein $R^1$ is an alkyloxycarbonyl group may be hydrolysed and then reacted with chlorosulfonyl isocyanate in order to form the nitrile.

The alkylation in step d) is carried out by addition of the 3-dimethylaminopropylhalogenide to the compound of formula VI ($R^1$=CN) in a proper solvent, such as an ether, preferably 1,2-dimethoxyethane (DME), THF, diglyme or diethylether, in the presence of a base, preferably lithium-diisopropylamine (LDA).

The process of the invention may be carried out with or without isolation of the intermediates.

Other reaction conditions, solvents, etc. are conventional conditions for such reactions and may easily be determined by a person skilled in the art.

The starting materials of formula IV may be prepared from the corresponding phthalide compound by reaction with a Grignard reagent of 4-halogen-fluorophenyl as exemplified with the magnesiumhalogenide in the following reaction scheme:

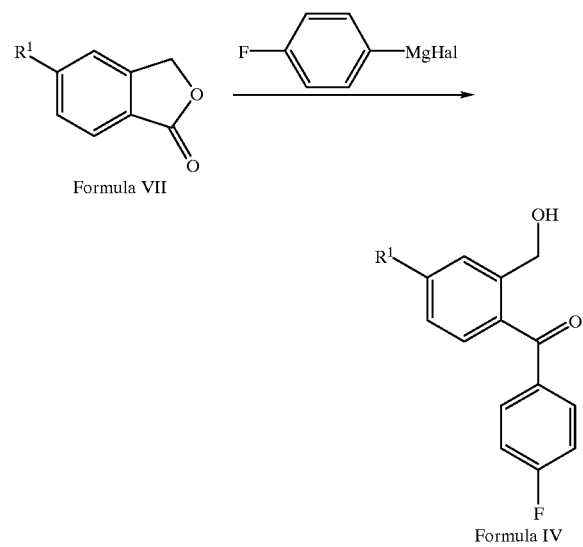

wherein $R^1$ is as defined above.

When $R^1$ is a cyano group, the starting materials of formula VII may be prepared as described in Tirouflet, J.; Bull. Soc. Sci. Bretagne 26, 1959, 35.

Other starting materials of formula IV may be prepared from 5-carboxyphtalide by reaction with thionyl chloride and then $C_{1-6}$ alkanol or $C_{1-6}$ alkylamine. 5-carboxyphtalide is commercially available and may be prepared by well known procedures (Tirouflet, J.; Bull. Soc. Sci. Bretagne 26, 1959, 35).

In a preferred embodiment of the invention, $R^1$ is cyano.

In another embodiment of the invention, $R^1$ is $C_{1-6}$ alkyloxycarbonyl, the $C_{1-6}$ alkyl group being preferably ethyl, propyl, or butyl, preferably ethyl, 2-propyl or t-butyl.

In yet another embodiment of the invention, $R^1$ is $C_{1-6}$ alkylaminocarbonyl, the $C_{1-6}$ alkyl group being preferably ethyl, propyl, or butyl, preferably ethyl, 2-propyl or t-butyl, most preferably t-butyl.

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted Keith either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilization of the solution and filling in suitable ampules or vials. Any suitable additive conventionally used in the art may be added, such as tonicity agents, preservatives, antioxidants, etc.

EXAMPLES

The invention is further illustrated by the following examples.

Example 1

(4-Cyano-2-hydroxymethylphenyl)(4-fluorophenyl) methanol

A solution of 4-fluorophenylmagnesium bromide, prepared from 4-fluorobromobenzene (605 g, 3.45 mole) and magnesium turnings (107 g, 4.4 mole) in dry THF (1200 mL), is added dropwise to a suspension of 5-cyanophthalid (500 g, 3.14 mole) in dry THF (3000 mL). The temperature is kept below 5° C. After the addition is complete, the reaction mixture is stirred the night over at room temperature.

Ethanol (4500 mL) is added to the reaction mixture and NaBH$_4$ (238 g, 6.30 mole) is added to the mixture in portions of 50 grams and is stirred the night over at room temperature. About 2/3 of the solvents is removed in vacuo and water (4000 mL) is added to the reaction mixture. The resulting solution is extracted with EtOAc (2×500 mL). Evaporation of the solvents leaves a crude title compound (780 g) as an oil which is deemed pure enough for further reaction.

A pure sample is obtained after column chromatography on silica gel using EtOAc/n-Heptane (1/1) as eluent. The title compound is obtained as crystals after evaporation of the eluent. DSC onset: 116.5° C.

$^1$H NMR (DMSO-d$_6$, 500 MHz): 4.42 (1H, dd J=13 Hz, J=5 Hz), 4.53 (1H, dd J=13 Hz, J=5 Hz), 5.45 (1H, t J=5 Hz), 5.98 (1H, d J=3 Hz), 6.14 (1H, d J=3 Hz), 7.15 (2H, J=10 Hz), 7.35 (2H, m), 7.74 (1H, d J=8.5 Hz), 7.77 (1H, d J=8.5 Hz), 7.83 (1H, s).

Anal. calcd. for C$_{15}$H$_{12}$N$_1$F$_1$O$_2$; C, 70.02; H, 4.71; N, 5.45. Found C, 70.01; H, 4.71; N, 5.51.

1-(4-fluorophenyl)-1,3-dihydroisobenzofuran-5-carbonitrile

Crude (4-cyano-2-hydroxymethylphenyl)(4-fluorophenyl)methanol (700 g) is dissolved in H$_3$PO$_4$ (60%, 3000 mL) and the solution is heated to 80° C. for 3 hours. Toluene (1000 mL) is added and the phases are separated. The aqueous phase is further extracted with toluene (1000 mL). The toluene phases are joined and the solvents are removed in vacuo. The remaining crystals are recrystallized from EtOH (99%). Yield 219 g (29%). DSC onset: 97° C.

$^1$H NMR (DMSO-d$_6$, 500 MHz): 5.15 (1H, d J=12.5 Hz), 5.32 (1H, d J=12.5 Hz), 6.27 (1H, s), 7.21 (2H, t J=10 Hz), 7.25 (1H, d J=8.5 Hz), 7.40 (2H, m), 7.71 (1H, d J=8.5 Hz), 7.90 (1H, s).

Anal. calcd. for C$_{15}$H$_{10}$N$_1$F$_1$O$_1$; C, 75.30; H, 4.22; N, 5.86. Found C, 75.01; H, 4.22; N, 5.83.

1-(3-Dimethylaminopropyl)-1-(4-fluorophenyl)-1,3-dihydroisobenzofuran-5-carbonitrile n-BuLi (1.6 N in hexane, 320 mL) is added to diisopropylamine (55 g, 0.5 mole) dissolved in DME (150 mL) at −50° C. over a nitrogen atmosphere. 1-(4-fluorophenyl)-1,3-dihydroisobenzofuran-5-carbonitrile (62 g, 0.26 mole) is dissolved in DME (500 mL) and added dropwise while the temperature is kept below −40° C. After addition (45 min), the dark red solution is stirred for an additional period of 20 min. 3-Dimethylpropylchloride (100 g, 0.82 mole) is added in one portion at −50° C. and the cooling is removed. After 60 min, the solution is warmed to 50° C. for 120 min. The reaction mixture is poured onto ice water (1 L) and extracted with toluene (2×500 mL). The organic phase is extracted with HCl (4 N, 500 mL). The acid solution is made alkaline (pH=10) with NaOH (10 N) and extracted with toluene (500 mL) which is washed with water (3×200 ml). The toluene phase is dried anhydrous Na$_2$SO$_4$ (50 g), treated with active carbon and the solvents are removed in vacuo. The title compound (64–71 g, 76–84%) is obtained as an oil.

$^1$H NMR (DMSO-d$_6$, 500 MHz): 1.20 (1H, m), 1.30 (1 H, m), 2.00 (6H, s), 2.10–2.20 (4H, m), 5.12 (1H, d, J=13.5 Hz), 5.20 (1H, d, J=13.5 Hz), 7.13 (2H, t, J=8.5 Hz), 7.58 (2H, dt, J=1.2 Hz J=8.5 Hz), 7.70–7.78 (3H, m).

The oxalic acid salt is crystallized from acetone. DSC onset: 156° C. Anal. calcd. for C$_{22}$H$_{23}$N$_2$F$_1$O$_5$; C, 63.75: H, 5.60: N, 6.76. Found C, 61.60: H, 5.62: N, 6.63.

Example 2

(4-Ethoxycarbonyl-2hydroxymethylphenyl)(4-fluorophenyl)methanol

A solution of 4-fluorophenylmagnesium bromide, prepared from 4-fluorobromobenzene (21 g, 0.12 mole) and magnesium turnings (3.4 g, 0.14 mole) in dry THF (150 ml), is added dropwise to a suspension of 5-ethoxycarbonylphthalide (20.6 g, 0.1 mole) in dry THF (150 ml). The temperature is kept below 5° C. After the addition is complete, the reaction mixture is stirred the night over at room temperature.

Ethanol (300 ml) is added to the reaction mixture and NaBH$_4$ (7.6 g, 0.2 mole) is added to the mixture in portions of about 1 gram and is stirred for 4 hours at room temperature. The solvents are removed in vacuo and ammonium chloride (sat. aq, 300 ml) is added to the remaining oil. The pH of the resulting solution is adjusted to 7.2 with aqueous 4 N HCl and extracted with EtOAc (2×100 ml). Evaporation of the solvents leaves a crude title compound as an oil (30 g) which is deemed pure enough for further reaction.

$^1$H NMR (DMSO-d$_6$, 500 MHz): 1.3 (3H, t J=7 Hz), 4.3 (2H, d J=7 Hz), 4.35–4.5 (2H, m), 4.55–4.65 (2H, m) 5.35 (1H, t J=3 Hz) 5.95 (1H, d J=3 Hz), 6.05 (1H, d J=3 Hz), 7.13 (2H, t J=10 Hz), 7.33 (2H, m), 7.64 (1H, d J=8.5 Hz), 7.90 (1H, d J=8.5 Hz), 8.10 (1H, s).

Ethyl 1-(4-fluorophenyl)-1,3-dihydroisobenzofuran-5-carboxylate

Crude (4-ethoxycarbonyl-2-hydroxymethylphenyl)(4-fluorophenyl)methanol (30 g) is dissolved in H$_3$PO$_4$ (60%, 250 ml) and the solution is heated to 80° C. for 1.5 hours. Water (300 ml) and EtOAc (100 ml) is added and the phases are separated. The aqueous phase is further extracted with EtOAc (100 ml). The organic phases are joined and the solvents are removed in vacuo. The yield of the remaining somewhat impure oil is 30 g.

$^1$H NMR (DMSO-d$_6$, 500 MHz): 1.3 (3H, t J=7 Hz), 4.3 (2H, d J=7 Hz), 5.17 (1H, d J=13 Hz), 5.35 (1H, d J=13 Hz), 6.25 (1H, s) 7.20 (3H, d+t J=8.5 Hz J=10 Hz), 7.41 (2H, m), 7.86 (1H, d J=8.5 Hz), 7.97 (1H, s).

1-(4-fluorophenyl)-1,3-dihydroisobenzofuran-5-carboxylic acid

Crude ethyl 1-(4-fluorophenyl)-1,3-dihydroisobenzofuran-5-carboxylat (30 g) is dissolved in EtOH (96%, 150 ml) and aqueous 2N NaOH (150 ml). The solution is refluxed for 1 hour. ½ of the volume is removed in vacuo. The aqueous phase is extracted with EtOAc (2×100 ml). The aqueous phase is made acidic (pH=1, conc. HCl) and after cooling to 5° C. the white crystals are filtered off. Yield 16 g. Overall yield is 66% starting from 5-ethoxycarbonylphthalide. Mp 187–190° C.

$^1$H NMR (DMSO-$d_6$, 500 MHz) 5.15 (1H, d J=13 Hz), 5.33 (1H, d J=13 Hz), 6.23 (1H, s) 7.18 (3H, d+t J=8.5 Hz J=10 Hz), 7.40 (2H, m), 7.84 (1H, d J=8.5 Hz), 7.94 (1H, s) 12.95 (1H, bs).

The compound obtained is then converted to the corresponding cyano compound which again is alkylated as described in Example 1.

What is claimed is:

1. A method for the preparation of citalopram comprising the steps of (a) reduction of a compound of Formula IV

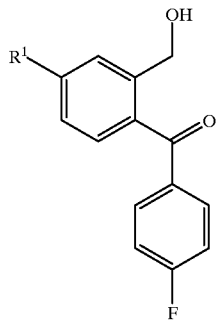

wherein $R^1$ is cyano, $C_{1-6}$ alkyloxycarbonyl or $C_{1-6}$ alkylaminocarbonyl, (b) effecting ring closure of the resulting compound of Formula V

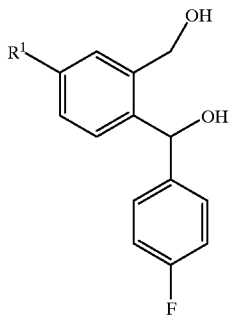

wherein $R^1$ is as defined above, thereby obtaining a compound of Formula VI

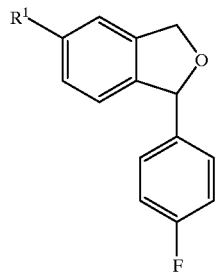

wherein $R^1$ is as defined above; and then (c) if $R^1$ is cyano, using the compound of Formula VI directly in step (d) and if $R^1$ is $C_{1-6}$ alkyloxycarbonyl or $C_{1-6}$ alkylaminocarbonyl, converting the compound of Formula VI to the corresponding compound wherein $R^1$ is cyano; and (d) alkylating the resulting 5-cyano compound of formula VI with 3-dimethylaminopropylhalogenide in basic conditions, thereby obtaining citalopram,

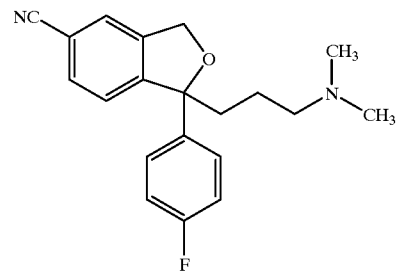

which is isolated as a base or a pharmaceutically acceptable salt thereof.

2. The method of claim 1 wherein $R^1$ is CN.

3. The method of claim 1 wherein $R^1$ is $C_{1-6}$ alkyloxycarbonyl.

4. The method of claim 1 wherein $R^1$ is $C_{1-6}$ alkylaminocarbonyl.

5. The method of claim 3 wherein said $C_{1-6}$ alkyl moiety of said $C_{1-6}$ alkyloxycarbonyl is selected from the group consisting of ethyl-, propyl-, or butyl.

6. The method of claim 4 wherein said $C_{1-6}$ alkyl moiety of said $C_{1-6}$ alkylaminocarbonyl is selected from the group consisting of ethyl, propyl and butyl.

7. The method of claim 1 wherein the reduction of the compound of Formula IV is performed by use of NaBH$_4$ in an alcohol under basic conditions.

8. The method of claim 1 wherein the ring closure of the compound of Formula V is effected by acidic ring closure performed by an inorganic acid or an organic acid.

9. The method of claim 8 wherein said acidic ring closure is performed by an inorganic acid selected from the group consisting of sulfuric acid and phosphoric acid.

10. The method of claim 8 wherein said acidic ring closure is performed by an organic acid selected from the group consisting of methylsulfonic acid, p-toluenesulfonic acid and trifluoroacetic acid.

11. The method of claim 1 wherein the ring closure of the compound of Formula V is performed by a basic ring closure via a labile ester, optionally with simultaneous esterification and addition of base.

12. The method of claim 11 wherein the labile ester is the methane sulfonyl, p-toluene sulfonyl, 10-camphorsulfonyl, trifluoroacetyl or trifluoromethanesulfonyl ester and the base is triethyl amine, dimethylaniline or pyridine.

13. The method of claim 3 wherein the conversion of the $C_{1-6}$ alkyloxycarbonyl to cyano is performed via the corresponding amide group.

14. The method of claim 13 wherein the reaction of $C_{1-6}$ alkoxycarbonyl to amide is carried out by hydrolysis with an acid or a base, subsequent conversion to acid chloride and amidation by reaction with ammonia or an alkylamine.

15. The method of claim 14 wherein the hydrolysis is performed by use of an acid selected from the group consisting of HBr, HCl and HBr/acetic acid.

16. The method of claim 14 wherein the hydrolysis is performed by use of a base selected from the group consisting of $K_2CO_3$, NaOH and KOH.

17. The method of claim 13 wherein the reaction of $C_{1-6}$ alkyloxycarbonyl to amide is carried out by reaction of the ester with ammonia or an alkylamine under pressure and heating.

18. The method of claim 4 wherein the amide is converted to the cyano group by reaction with a dehydrating agent.

19. The method of claim 18 wherein said dehydration agent is selected from the group consisting of thionyl chloride and phosphorous pentachloride.

20. The method of claim 1 wherein the 3-dimethylaminopropylhalogenide in step (d) is the chloride, bromide or iodide.

21. The method of claim 1 wherein the alkylation of step (d) is carried out in an ether.

22. The method of claim 21 wherein said ether is selected from the group consisting of 1,2-dimethoxyethane, THF, diglyme and diethylether.

23. The method of claim 1 wherein the alkylation in step (d) is carried out in the presence of a base.

24. The method of claim 23 wherein said base is a lithiumdiisopropylamine.

25. The method of claim 1 wherein the starting material of formula IV is prepared from the corresponding phthalide compound by reaction with a Grignard reagent of 4-halogen-fluorophenyl.

26. The method of claim 1 wherein $R^1$ is cyano, the starting material of formula IV is prepared from the corresponding phthalide compound by reaction with a 4-fluorophenylmagnesiumhalogenide, the reduction in (a) is performed by $NaBH_4$ in an alcohol, the ring closure in (b) is effected by an inorganic acid, and the alkylation in (d) is carried out by use of dimethylaminopropylchloride in an ether in the presence of lithiumdiisopropylamine.

27. A compound of Formula V

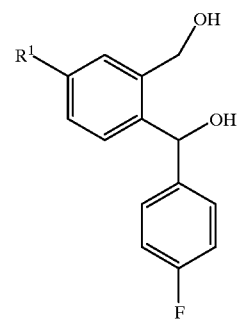

wherein $R^1$ is selected from the group consisting of CN, $C_{1-6}$ alkyloxycarbonyl and $C_{1-6}$ alkylaminocarbonyl.

28. A compound of Formula VI

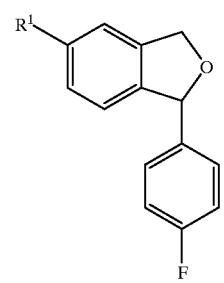

wherein $R^1$ is selected from the group consisting of $C_{1-6}$ alkyloxycarbonyl and $C_{1-6}$ alkylaminocarbonyl.

29. A method for the preparation of citalopram comprising alkylating a compound of formula VI

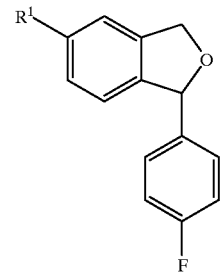

wherein $R^1$ is selected from the group consisting of CN, $C_{1-6}$ alkyloxycarbonyl and $C_{1-6}$ alkylaminocarbonyl, with 3-dimethyl-aminopropylhalogenide in basic conditions in which the reaction is carried out in an ether in the presence of lithiumdiisopropylamine.

30. The method of claim 29 wherein said ether is selected from the group consisting of 1,2-dimethoxyethane, THF, diglyme and diethylether.

* * * * *